US005300090A

United States Patent [19]

Primic

[11] Patent Number: 5,300,090

[45] Date of Patent: Apr. 5, 1994

[54] EXERCISE MACHINE

[75] Inventor: Heinrich L. Primic, Port Elizabeth, South Africa

[73] Assignee: Challenge Machinery (Proprietary) Ltd., Cape Province, South Africa

[21] Appl. No.: 940,311

[22] Filed: Sep. 3, 1992

[51] Int. Cl.[5] ........ A61F 5/00

[52] U.S. Cl. ........ 601/26; 606/243; 606/245; 606/242; 74/371; 601/35

[58] Field of Search ........ 128/25 R, 25 C; 606/241-245; 434/254; 482/55, 56, 115; 74/371, 373

[56] References Cited

U.S. PATENT DOCUMENTS

| | | | |
|---|---|---|---|
| 1,400,546 | 12/1921 | Holme | 606/245 |
| 2,032,303 | 2/1936 | Orgitano | 128/25 R |
| 2,893,380 | 7/1959 | Walker et al. | 128/25 R |
| 2,949,911 | 8/1960 | Kennard et al. | 128/25 R |
| 3,060,926 | 10/1962 | May | 128/25 R |
| 4,637,607 | 1/1987 | McArthur | 482/115 |
| 4,656,886 | 4/1987 | Edwards | 74/371 |
| 5,098,088 | 3/1992 | Cohen et al. | 128/25 R |
| 5,109,722 | 5/1992 | Hufnagle et al. | 74/371 |
| 5,123,916 | 6/1992 | Riddle et al. | 606/242 |
| 5,142,944 | 9/1992 | McArthur et al. | 74/371 |

*Primary Examiner*—Richard J. Apley
*Assistant Examiner*—Jeanne M. Mollo

[57] ABSTRACT

A multiple movement exercising machine is powered by an electric drive motor which is used to effect movement of various exercising components. The drive motor drives a shaft on which a plurality of pulleys are rotationally mounted. A selector arrangement is used to connect a selected one of the pulleys within the shaft so that the pulley rotates with the shaft and drives an exercising component linked to that pulley by a belt. One end of the machine is preferably pivotable relative to the remainder of the machine about a vertical pivot axis. The extent of pivotal movement is preferably selectably variable.

10 Claims, 7 Drawing Sheets 6
33
34
35
36
37
38
70
32
33
31
30
60
30
58
59
61
62
63
65
5

EXERCISE MACHINE

BACKGROUND TO THE INVENTION

This invention relates to an exercise machine of the type which can be used passively, that is, the machine is powered to perform a range of movements and enables a user to sit or lie on the machine in order to exercise whilst the machine is performing those movements.

Passive exercising machines of this type are used extensively by invalids and others requiring physiotherapy or like treatment. Others use this type of machine to improve muscle tone. The machines are particularly useful for the treatment of persons suffering from spinal cord damage to provide exercise for muscles which would otherwise not be worked. Many institutions which provide this type of exercise facility for patients have a range of machines, each of which is able to perform a single exercise. The invalid will then need to be moved from one machine to another in order to have a range of muscles worked. This is inconvenient where the invalid is unable to walk since each time he has to be helped off one machine and onto another. Also, having a range of machines like this requires substantial floor space which many institutions simply do not have.

At least some prior art machines do not adequately assist the user to exercise certain muscles, particularly hip and leg muscles. Also, many prior art machines are noisy in operation on account of the type of mechanism which operates the exercising feature on the machine. Most prior art machines are not capable of performing more than a limited number of exercises without having to be re-adjusted or re-set.

SUMMARY OF THE INVENTION

According to a first aspect of the invention there is provided a multiple movement powered exercising machine comprising a frame, an electric drive motor mounted on the frame, a drive shaft mounted for rotation on the frame and adapted to be rotationally driven by the motor, a series of pulleys mounted on the drive shaft each of which is capable of either being rotationally driven by the shaft during shaft rotation or having the shaft rotate relative thereto, and selector means for interconnecting the shaft and a selected pulley to cause the selected pulley to rotate with the shaft, said pulleys each being connected by a respective drive belt to a respective exercise component on the machine.

It is preferred that the selector means operates automatically in order to select each of a plurality of said pulleys sequentially. The selector means may comprise a micro-processor, a selector motor operable by said micro-processor, and a selector key movable by said selector motor and engageable with each of said pulleys selectively to cause the drive motor to connect to any one of said slave pulleys through said shaft.

According to a second aspect of the invention there is provided an exercise machine comprising a generally elongate frame having a generally horizontal and planar upper surface adapted to support a person lying thereon, one end of the frame being adapted to generally support the head of the person and the other end of the frame adapted to generally support the legs of the person, said other end of the frame being connected to the remainder of the frame through a pivot assembly which has a generally vertical pivot axis and permits said other end to pivot back and forth about said pivot axis through a preselected arc.

Said other end may also incorporate a pair of generally elongate leg supports each of which is connected at one end thereof to the frame through a pivot arrangement which has a generally horizontal pivot axis located in a zone of the frame where the hips of a person lying on the frame would be situated in use, the other end of the leg supports being adapted to be moved above and below a horizontal plane which includes the horizontal pivot axis. Preferably the two leg supports are capable of being selectively raised and lowered either together or alternatively, at the option of the user.

An embodiment of the invention is described in detail in the following passages of the specification which refer to the accompanying drawings. The drawings, however, are merely illustrative of how the invention might be put into effect, so that the specific form and arrangement of the various features shown is not to be understood as limiting on the invention.

DETAILED DESCRIPTION OF PREFERRED EMBODIMENT

Figure 1:
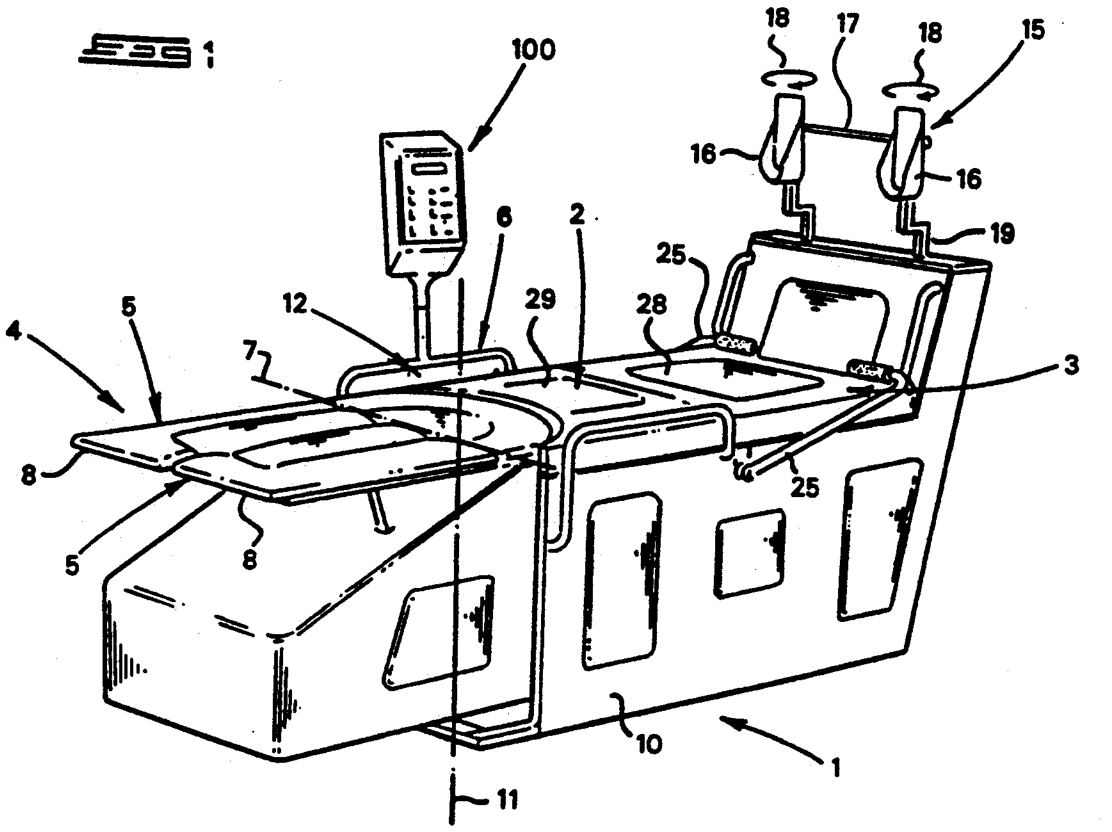
FIG. 1 shows a perspective view of an exercising machine according to the invention.
Figure 2:
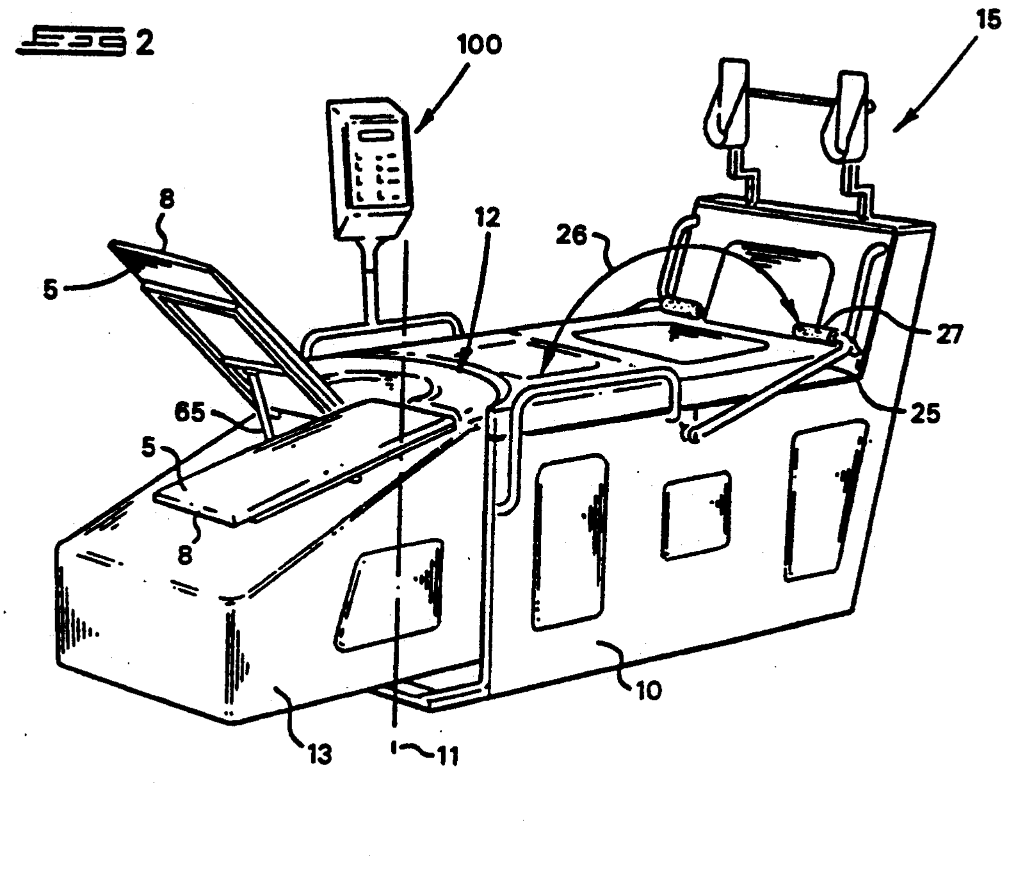
FIG. 2 shows a similar view to that of FIG. 1 but with one leg support in a raised position and the other leg support in a lowered condition.
Figure 3:
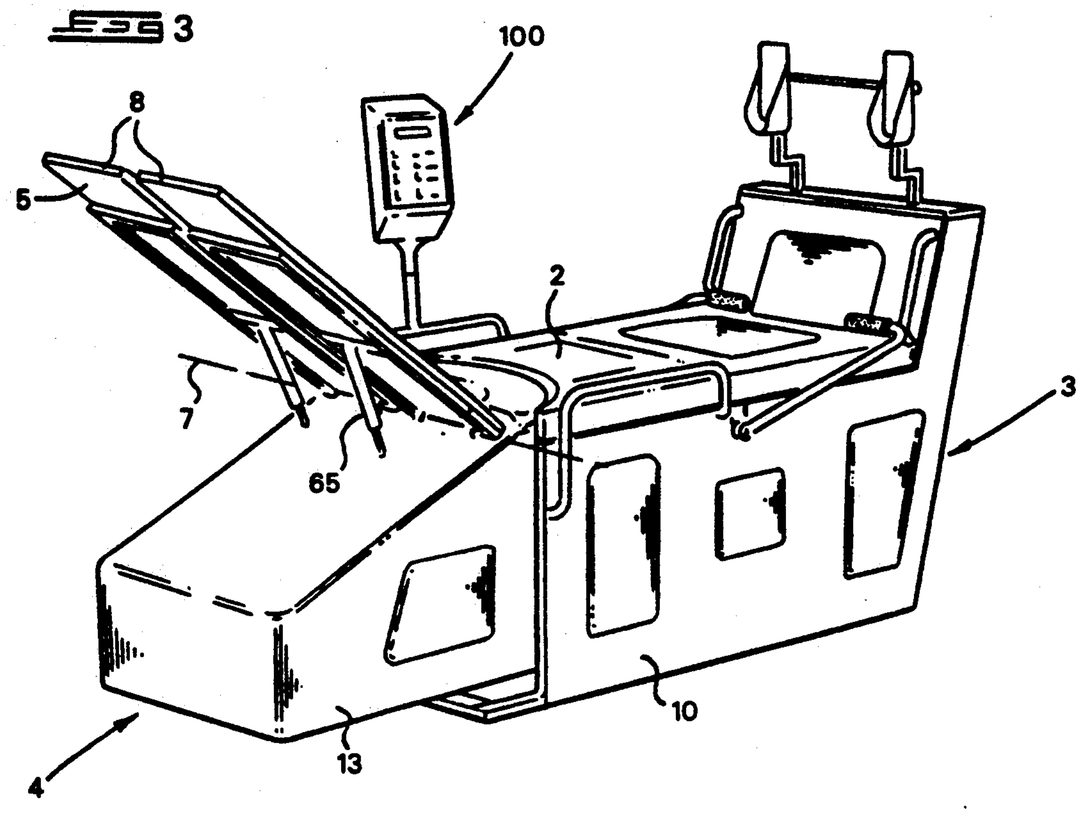
FIG. 3 depicts a similar view to that of FIG. 1 but with both leg supports in a raised condition.

Referring initially to FIGS. 1 to 4, an exercising machine 1 is of generally rectilinear form and has an upper surface 2 which is adapted to support a person lying thereon and is generally planar and horizontal. Thus, the upper surface 2 will be of generally elongate form and dimensioned to receive an adult person lying thereon in comfort. One end 3 of the machine 1 is where the head of a person lying on the upper surface 2 will generally be located (although this will not be so for all exercises which can be conducted on the machine). The other end 4 of the machine will generally be where the feet of a person lying on the machine will be located. The upper surface 2 at the said other end 4 of the machine is defined by two generally elongate planar slats 5 which are hinged to the central region 6 of the upper surface 2 through a pivot, the axis of which is indicated at numeral 7. These slats 5 will be capable of being raised and lowered either together as indicated in FIG. 3 or oppositely in synchronisation as indicated in FIG. 2. As will be clear from FIG. 2, the free ends 8 of the slats 5 will be capable of moving above and below the horizontal plane in which the pivot axis 7 lies. Thus, the free ends 8 of each slat can move below that horizontal plane or above that horizontal plane and the machine 1 will include power means to achieve this movement.

Figure 4:
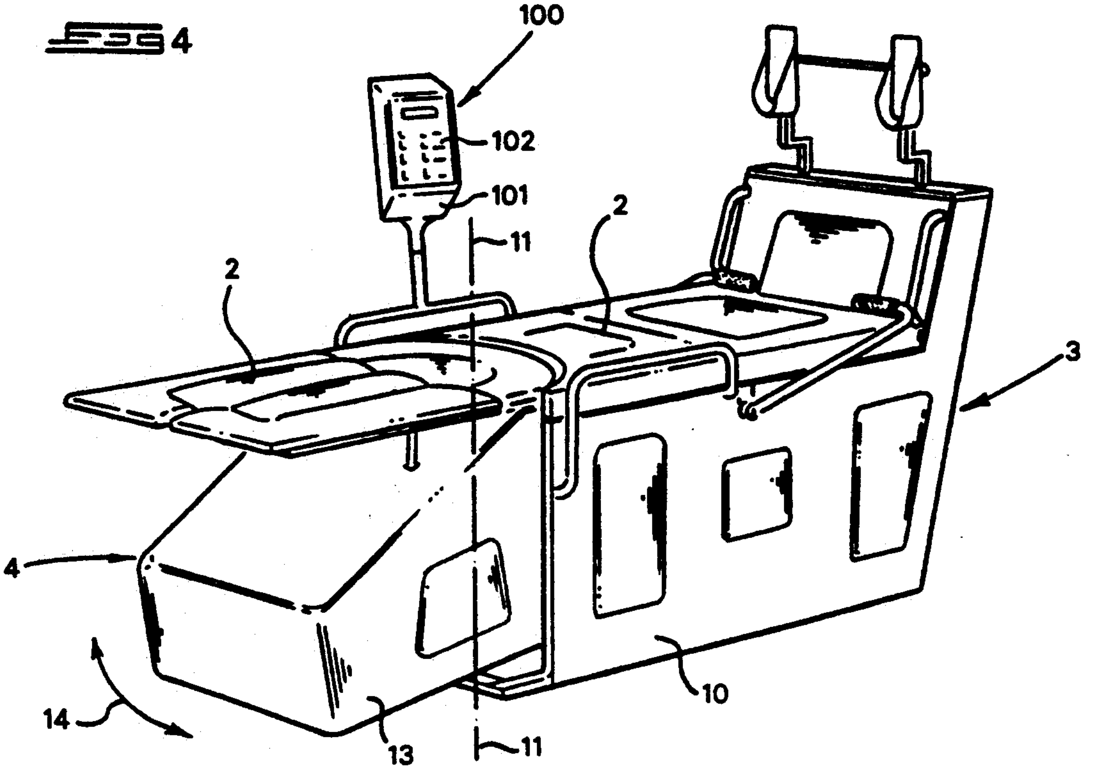
FIG. 4 depicts a similar view to that of FIG. 1 with the nose-cone portion of the exercising machine in a laterally offset position.
Figure 5:
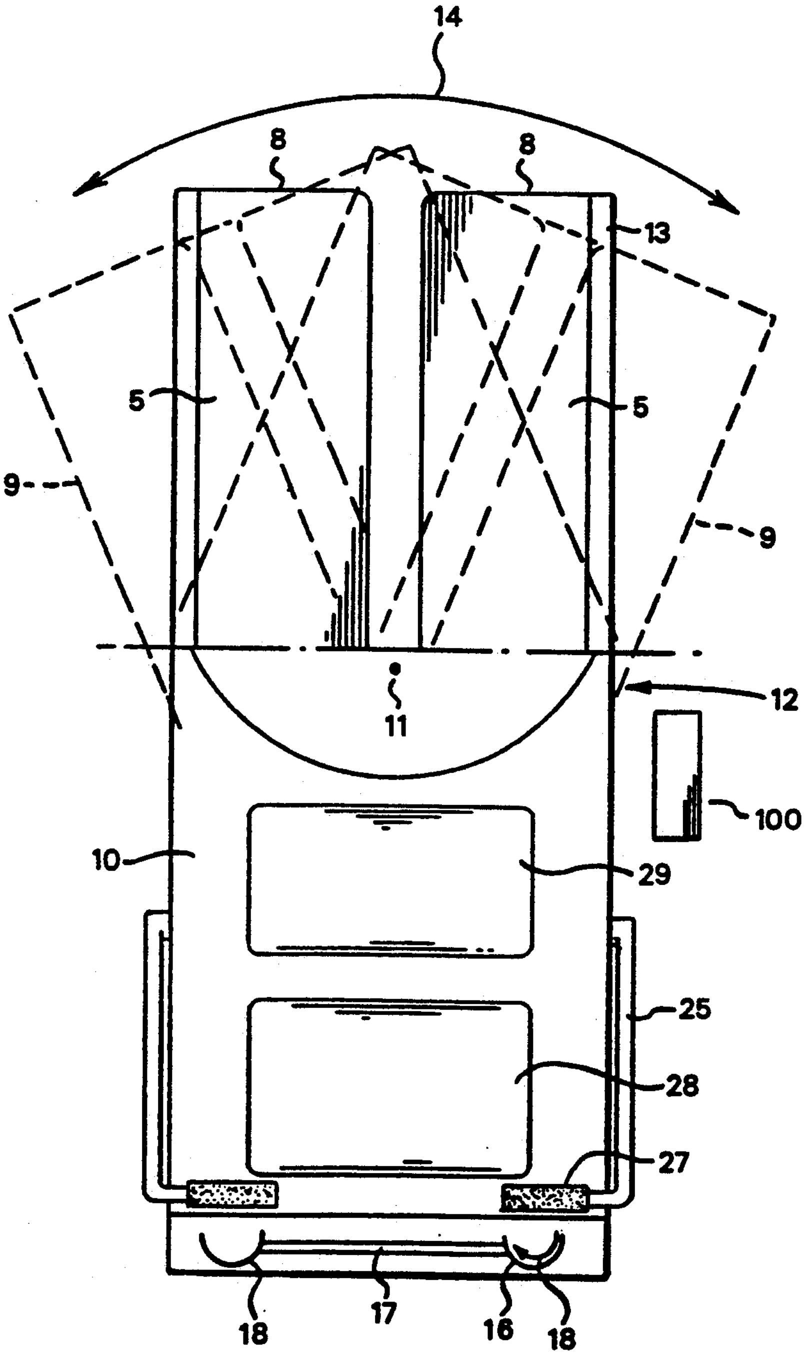
FIG. 5 depicts a plan view of the machine shown in FIGS. 1 to 4.

Said other end 4 of the machine 1 is connected to the remainder 10 of the machine through a vertical pivot arrangement, having a vertical pivot axis 1 1, which will be described in more detail herebelow. FIGS. 4 and 5 show the manner of movement of the other end 4 of the machine relative to the remainder 10. The vertical pivot axis 11 will pass through the region 12 on the upper surface 2 where generally the hips of a user lying on the surface 2 will be located. The machine 1 is preferably configured having a nose cone 13, dotted lines 9 indicating the extent of left and right lateral pivoting movement which is able to pivot laterally to both sides of the functional centre line of the machine. FIG. 5 depicts the degree of movement of this nose cone 13. The slats 5 are connected to the nose cone 13 so that they will also pivot left and right as the nose cone 13 is pivoted in use. It will be appreciated that a person lying on the upper surface 2 whilst the nose cone 13 is pivoting left and right will have his or her legs pivoted relative to their body through an arc indicated by arrow 14. This movement will tend to exercise the hip and buttock muscles and upper thigh muscles as well as the lower back and abdomen region. Such passive exercising of these muscles will greatly enhance the strength thereof in a non-stressful manner and this will be particularly useful for those persons who have lost the use of their legs or require strengthening of these muscles. Similarly, the raising and lowering of the slats 5 about the pivot axis 7 will stretch and exercise various muscles in the hip and upper leg region.

The machine has a series of other exercises associated therewith. A pair of lower leg and foot exercisers 15 are located near said one end 3 of the machine. These exercisers 15 include feet pads 16 which are tied together by a bar 17 and rotate in a circular manner as indicated by arrows 18. The feet pads 16 are mounted on cams 19 which are rotatable in order to rotate the feet pads 16.

The machine also includes a pair of arm exercising bars 25 which are movable through an arc indicated by numeral 26 and each of which have a handle 27 which a user will hold in order to allow these bars to be held by a user and have his arms and shoulders exercised.

The machine also includes a pair of pads 28 and 29 which support the shoulders and back respectively of a person lying on the upper surface 2. These pads are able to move back and forward in a reasonably rapid cycle in a horizontal plane in the longitudinal direction of the machine and thereby provide exercise for the shoulder and back of a user. These exercisers 28 and 29 tend to tone and strengthen the muscles of the upper back, upper arms, -abdomen and rib cage of the user and also tends to improve blood circulation of the user.

Figure 6:
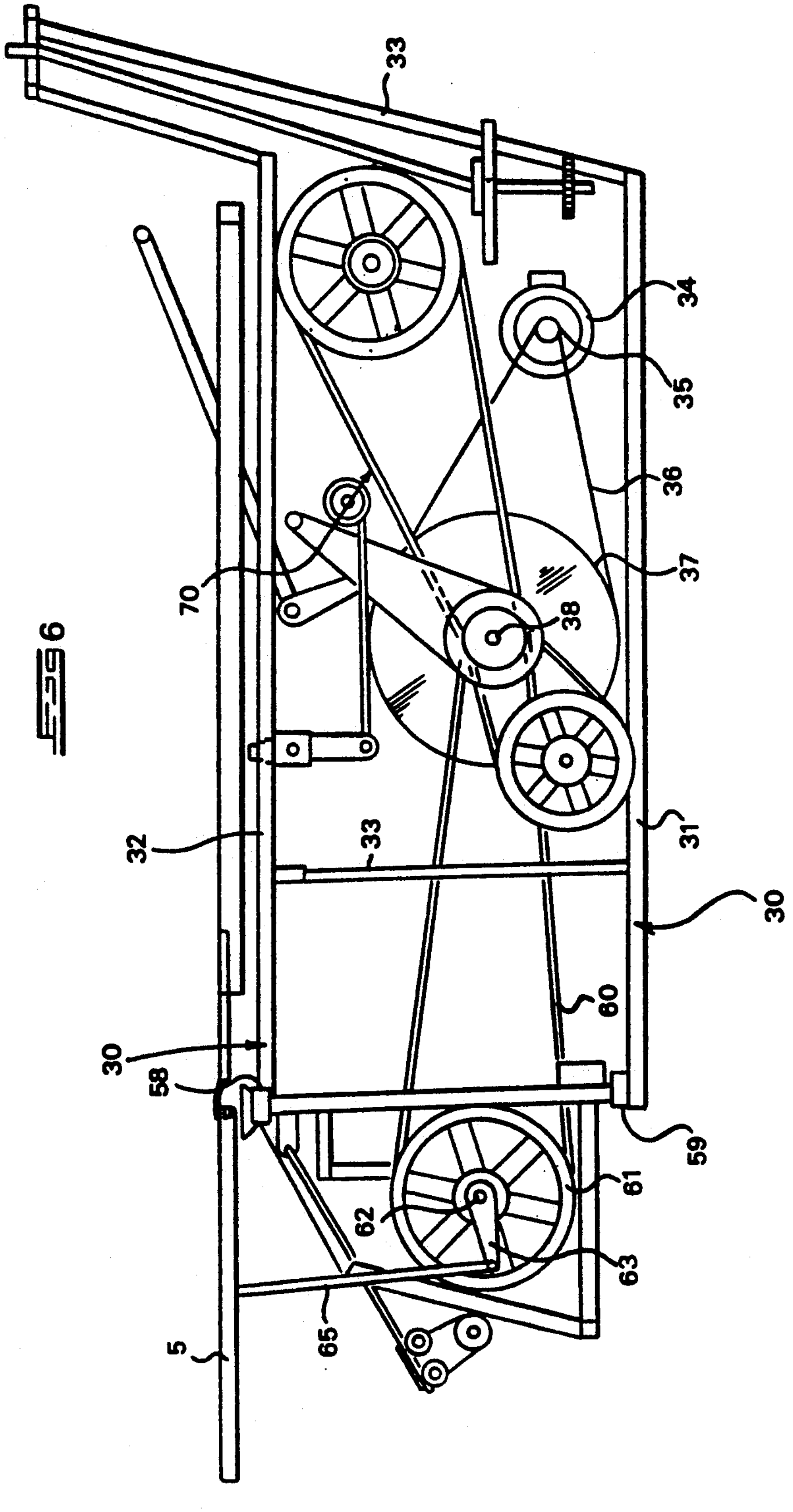
FIG. 6 depicts a side view of the internal mechanism and frame of the exercising machine shown in FIGS. 1 to 4.
Figure 7:
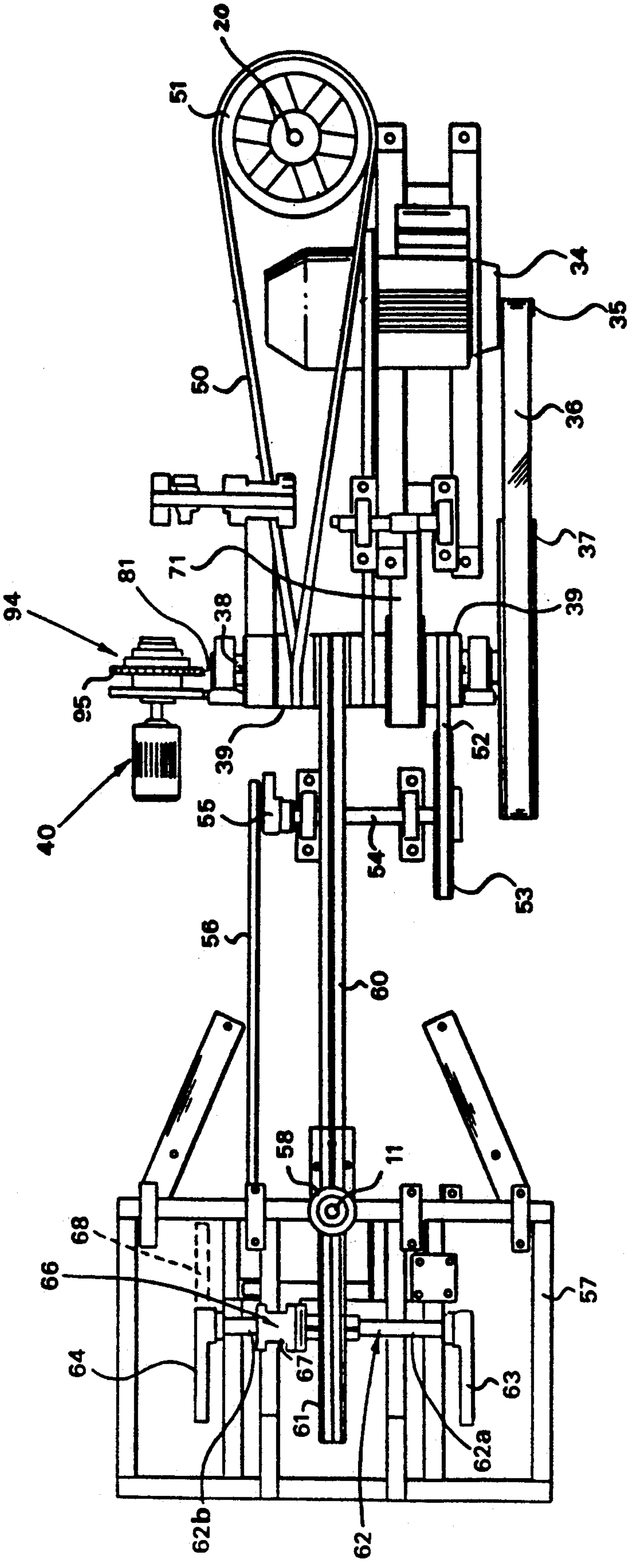
FIG. 7 shows a plan view of the drive system for the various exercising components.

The internal mechanism of the machine 1 is shown in diagrammatic form in FIGS. 6 and 7 of the drawings. As will be seen in FIG. 6, the machine includes a frame 30 which is formed by a base portion 31 and an upper portion 32. Vertical side bars 33 (not all of which are shown in the drawings) connect these two portions 31 and 32. The actual configuration of the frame is relatively unimportant although the frame, clearly, must support the machine components which effect the various exercise movements of the machine. The internal configuration of the machine is shown somewhat diagrammatically since the actual drive of the various components could be configured quite differently. A relatively simple mechanical arrangement couples the drive arrangement for the machine with the various exercise components and one skilled in the art will be able to construct a machine from the drawings and description set out below. The simplicity of the drive is indeed one of the features of the invention.

The moving components of the machine are driven by a main electric drive motor 34. This drive motor 34 may conveniently comprise an eight pole AC motor which is of variable speed, preferably rotating at speeds selectable between 0 and 3000 rpm. The drive motor 34 has an output shaft 35 which drives a belt 36 which in turn drives a main pulley 37. The drive ratio should be such that the main pulley 37 should be capable of rotating between 0 and 130 rpm, in other words, there should be a 1:23 reduction in speed between the drive motor 34 and the main drive pulley 37.

Figure 9:
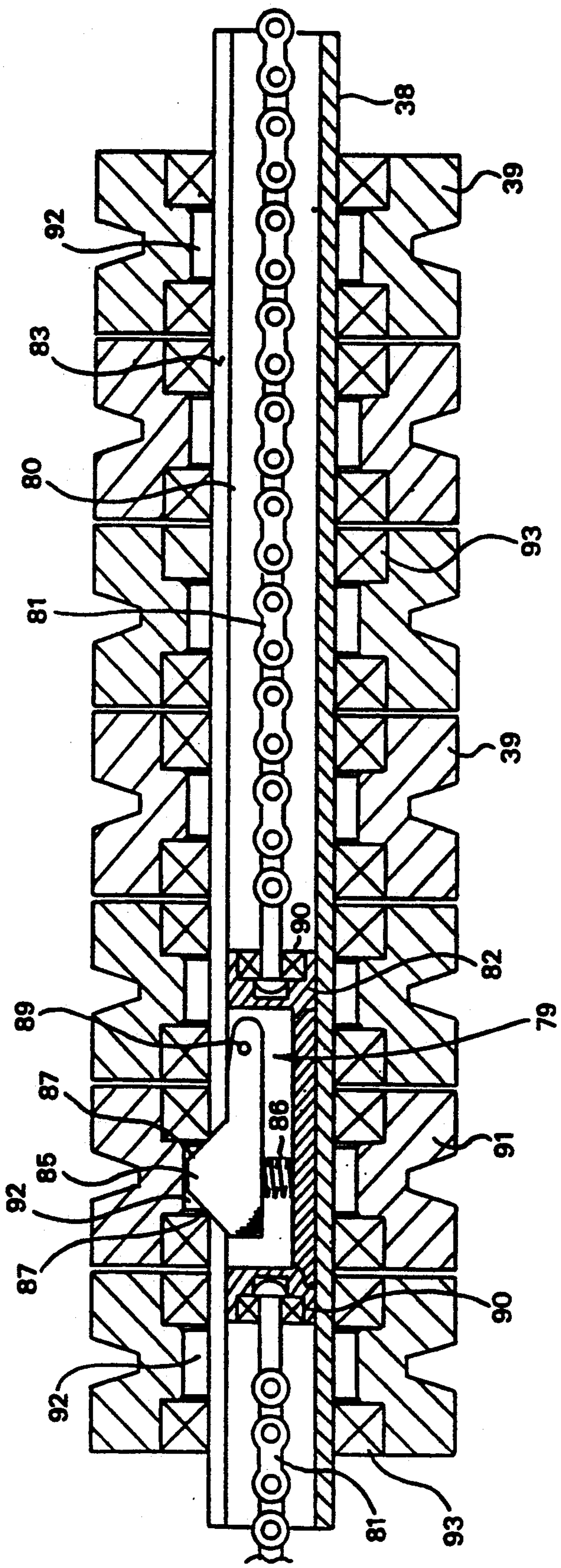
FIG. 9 shows a cross sectional view through the main drive shaft and selector assembly of the machine.

The main drive pulley 37 is connected to and drives a main drive shaft 38 which is shown in detail in FIG. 9 of the drawings. The main drive shaft 38 has a series of drive pulleys 39 mounted thereon. These drive pulleys 39 will not, in practice, all be driven simultaneously with the shaft 38. In the preferred arrangement, only one of those pulleys 39 will be driven by the shaft 38 and a selector arrangement 79 powered by a selector motor 40 will select which of the pulleys 39 is to be driven at any particular time. The selector arrangement 79 will be described in more detail herebelow. The drive pulleys will each be adapted to drive a slave pulley coupled to the different exercise components on the machine.

The drive shaft 38 as shown in FIG. 7 is adapted to drive a series of belts. Belt 50 is adapted to drive pulley 51 which in turn serves to rotate the shaft 20 coupled to the feet exercisers 15 (FIG. 1). Belt 52, drives pulley 53 which in turn rotates shaft 54 and cam 55. Cam 55 is connected to connecting rod 56 which in turn causes the left and right movement of the nose cone frame 57 about pivot axis 11. It will be noted that the nose cone frame 57 is connected to the remainder of the frame through bearings 58 and 59 which allow the left and right movement of the nose cone frame 57. Belt 60 is adapted to drive pulley 61 which in turn rotates shaft 62. Shaft 62 is adapted to drive a pair of cams 63 and 64 which in turn are adapted to raise and lower the slats 5 through connecting rods 65. The cams 63 and 64 either rotate together in a manner indicated in FIG. 7 of the drawings or one of the cams 63 or 64 is allowed to move through 180° by means of a slip coupling device 66. Dotted lines 68 indicate the position of cam 64 relative to cam 63 when the two cams have been allowed to move relative to each other through 180°. The shaft 62 is thus formed in two sections which are held together by slip coupling device 66. The slip coupling device 66 includes a sleeve 67 which holds the two sections (62*a* and 62*b*) of the shaft together.

The arm exercising bars 25 are driven by belt 70. Another pulley 39 will drive belt 71 for reciprocating pads 28 and 29.

Figure 8:
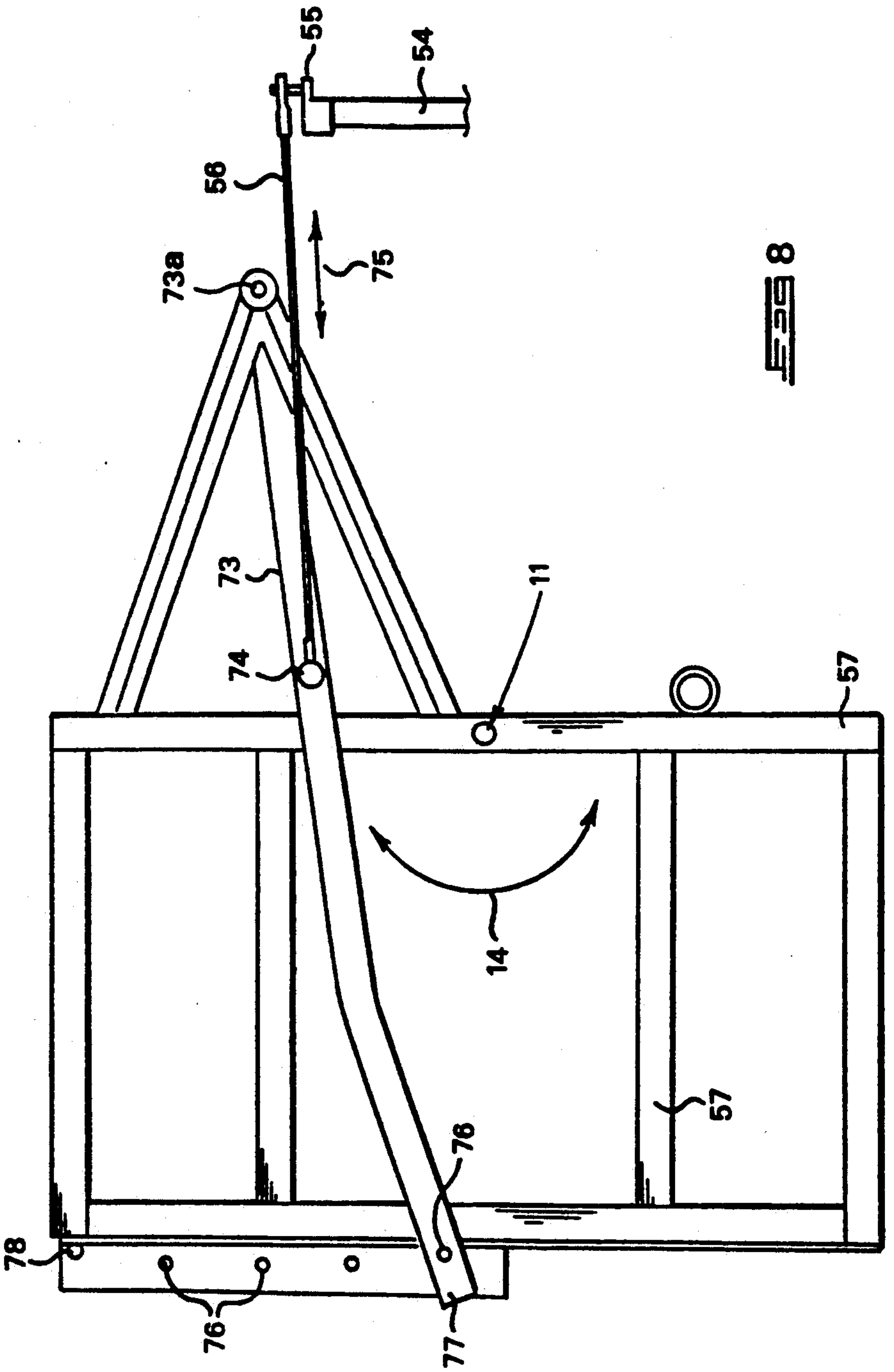
FIG. 8 depicts a plan view of the nose cone frame for the exercising machine shown in FIGS. 1 to 4.

The manner in which the nose cone frame can be caused to pivot left and right about pivot axis 11 is more clearly described with reference to FIG. 8 of the drawings. As shown, the connecting rod 56 is linked to a lever 73 through an pivot connection 74. As the cam 55 rotates the rod 56 is caused to move back and forth in a reciprocal manner as indicated by arrow 75. The lever 73 is pivotable about pivot point 73*a*. The frame 57 is proved with a series of connection positions indicated at numeral 76 and the end 77 of the lever is engageable in each of those positions. By locating the end 77 of the lever 73 in a different one of the connection positions 76 the frame 57 can be caused to move back and forth on pivot axis 11 to a greater or lesser extent. Clearly, the closer the articulated connection 74 is to the pivot axis 11 the greater will be the arc through which the nose cone frame 57 pivots during rotation of the shaft 54. Thus, when the end 77 of the lever 73 is located in adjustment position 78 there will be relatively little left and right movement of the nose cone during rotation of the shaft 57 whereas when the lever is in the position as shown in FIG. 8 there will be maximum left and right pivoting of the frame 57 relative to the remainder of the frame.

The manner in which the selector motor 40 selects which of the pulleys 39 will rotate at any one time will be clearly shown with reference to FIG. 9 of the drawings. As shown in FIG. 9 the shaft 38 is hollow and has a central passage 80 extending along the length thereof. In that passage 80 a chain 81 is moveable to drive a selector carriage 82 along the passage. The shaft 38 has a slot 83 extending along the length thereof and the selector carriage 82 includes a key 85 which runs in that slot 83. A spring 86 urges the key 85 outwardly through that slot 83. The key 85 has tapered edges 87 on each end thereof to facilitate movement of the key 85 back and forth along the length of the shaft 38. The key 85 is mounted to the selector carriage 82 through a pivot 89. The carriage 82 is able to rotate relative to the chain 81 through bearings 90. Thus, when the shaft 38 rotates the carriage 82 and key 85 will rotate with the shaft relative to the chain 81 which will not rotate. One of the pulleys 39, indicated at numeral 91 is engaged by the key 85. Each of the pulleys 39 has an inwardly directed transverse groove 92 which will be engaged by the key 85 when that key is in engagement with that particular pulley. Thus, for pulley 91, the key 85 has passed through the slot 83 in the shaft 38 and into engagement with the transverse groove 92 of that pulley. Pulley 91 will thus rotate with shaft 38 and key 85 in unison. All of the pulleys 39 are mounted on the shaft 38 on bearings 93. The bearings 93 permit the shaft 38 to rotate relative to each pulley 39. Thus, except for pulley 91, all the other pulleys 39 will be stationary whilst the shaft 38 is rotating, that is, they will not be driving the respective exercising device which that particular pulley is adapted to drive. At any one time, therefor, only one exercising component on the machine will be operating.

The motor 40 will drive a selector hub 94 having a sprocket 95 around which the chain 81 passes. Rotation of the motor 40 will rotate the sprocket 95 to move the carriage 82 along the length of the shaft 38 by pulling on the chain 81. The chain 81 will thus be linked to the motor 40 through the selector hub 95 such that rotation of the of the motor in one direction will move the carriage 82 in one direction whereas rotation of the motor in the opposite direction will move the chain and carriage 82 in the opposite direction. It is envisaged that the motor 40 will be a stepper motor capable of moving in either direction of rotation and be adapted to be rotated through a precise degree of angular rotation in order that each of the pulleys 39 can be selected as required.

The rotational speed of the drive motor 34 and the position of the selector motor 40 will be controlled by a control device indicated at numeral 100. That control device 100 will comprise a micro-processor 101 capable of operating the various elements of the machine in the required sequence and at the desired speed and for a selected time period. The control device 100 and micro-processor 101 will be operated by a key pad type control panel 102. It is envisaged that a user will be able to select, within a reasonable range of parameters, the speed with which any particular exercise will be conducted by varying the speed of the drive motor 34. Likewise, the user will be able to select which exercise will at any one time be conducted and the time period for which that exercise will be conducted. If a particular exercise is unsuited to a particular patient that exercise will be omitted from a sequence of exercises that the machine is capable of performing. Thus, the control device will control the exercise to be done, the time for which that exercise is done, and the speed in which the exercise is performed. Different patients will, of course, require different exercising patterns as is dictated by that patient's particular condition.

It will be appreciated that since each of the different exercise components is driven by a belt drive system, the whole machine will operate relatively smoothly. The selector device will be a convenient and efficient mechanism for transferring drive from the drive motor to the different components and shifting drive from one component to another. It will be a relatively simple matter for one skilled in the art to program the micro-processor in order to drive the exercise machine in the manner described above. Clearly the machine could easily be made to have additional or alternative exercise movements coupled to the drive motor.

It will be appreciated that the precise manner in which the different exercise components are constructed and driven has not been described herein in great detail. However, it will be clear that the exercise components are driven through pulleys 39 which drive belts for powering the exercise components. With that type of drive system one skilled in the art could easily achieve reciprocal, rotational, vibratory or pivoting movement as may be appropriate for a powered exercise machine of this type.

I claim:

1. A multiple movement powered exercising machine comprising: a frame, an electric drive motor mounted on the frame, a drive shaft mounted for rotation on the frame and adapted to be rotationally driven by the motor, a plurality of drive pulleys mounted on the drive shaft each of which is capable of either being rotationally driven by the shaft during shaft rotation or having the shaft rotate relative thereto, and selector means for interconnecting the shaft and a selected drive pulley to cause the selected drive pulley to rotate with the shaft, said drive pulleys each being connected by a respective drive belt to a respective slave pulley coupled to an exercise component on the machine, the selector means being automatically operable in order to select each of said plurality of drive pulleys in a predetermined sequence, the selector means further including a micro-processor, a selector motor operable by said micro-processor, and a selector key movable by said selector motor and selectively engageable with each of said drive pulleys to cause the drive motor to connect to any one of said slave pulleys through said drive shaft, the drive shaft comprising a hollow tubular wall defining a central passage within which the selector key is axially movable, said wall having one or more openings therethrough through which the selector key projects to engage a respective one of said drive pulleys, said selector key being movable within said central passage by a laterally flexible member connected to and driven by said selector motor, said selector key being rotatable with said drive shaft relative to said laterally flexible member.

2. A machine according to claim 1 wherein the drive motor is a variable speed motor, and the micro-processor is adapted to control the speed of the motor.

3. A machine according to claim 1 wherein said frame comprises a generally elongated structure having a horizontal and planar upper surface adapted to support a person lying thereon, one end of the frame being adapted to generally support the head of the person and the other end of frame adapted to generally support the legs of the person, said other end of the frame being connected to the remainder of the frame through a pivot assembly which has a generally vertical pivot axis and permits said other end to oscillate back and forth about said pivot axis through a preselected arc, said other end of the frame being connectable to the drive motor through a drive connection for causing continuous oscillation of said other end during operation of the drive motor.

4. A machine according to claim 3 wherein said either end incorporates a pair of generally elongate leg supports each of which is connected at one end thereof to the frame through a pivot arrangement which has a generally horizontal pivot axis located in a zone of the frame where the hips of a person lying on the frame would be situated in use, said leg supports having a distal end from said pivot arrangement, said distal end being adapted to be moved above and below a horizontal plane which includes the horizontal pivot axis, said leg supports being connectable to the drive motor and adapted to be raised and lowered repeatedly during operation of the drive motor.

5. A machine according to claim 4 wherein said leg supports can be selectively raised and lowered by the drive motor, either together or alternatively, at the option of the user.

6. A machine according to claim 3 wherein the drive connection is adjustable, adjustment of the drive connection being adapted to vary the pre-selected arc through which said other end oscillates about the vertical pivot axis relative to the remainder of the frame.

7. A machine according to claim 3 wherein movement of said pivoting of said other end is controlled by a micro-processor.

8. A machine according to claim 1 wherein the selector key is pivotally mounted to a carriage which is axially movable within said central passage, said carriage having a rotatable bearing assembly mounted in the respective opposite ends thereof, the flexible member being connected to the bearing assemblies for rotation relative to the flexible member.

9. A machine according to claim 8 wherein a spring is located on the carriage and the spring is located between the carriage and the selector key to urge the selector key into engagement with the selected drive pulley.

10. A machine according to claim 1 wherein the laterally flexible member is an endless chain which extends through the length of the shaft and loops around and is in meshed engagement with a toothed wheel driven by the selector mode.

* * * * *